US012653292B2

(12) United States Patent
Lattanzi et al.

(10) Patent No.: US 12,653,292 B2
(45) Date of Patent: Jun. 16, 2026

(54) COSMETIC PRODUCT WITH SURFACE DECORATION OF DYNAMIC IMAGES

(71) Applicant: INTERCOS S.p.A., Milan (IT)

(72) Inventors: Giuseppe Lattanzi, Limbiate (IT); Giovanni Venturelli, Paderno Dugnano (IT)

(73) Assignee: INTERCOS S.p.A., Milan (IT)

( * ) Notice: Subject to any disclaimer, the term of this patent is extended or adjusted under 35 U.S.C. 154(b) by 298 days.

(21) Appl. No.: 18/282,137

(22) PCT Filed: Jun. 21, 2021

(86) PCT No.: PCT/IB2021/055445
    § 371 (c)(1),
    (2) Date: Sep. 14, 2023

(87) PCT Pub. No.: WO2022/195339
    PCT Pub. Date: Sep. 22, 2022

(65) Prior Publication Data
    US 2025/0280940 A1     Sep. 11, 2025

(30) Foreign Application Priority Data

Mar. 15, 2021    (IT) ........................ 102021000006122

(51) Int. Cl.
| | |
|---|---|
| *A45D 33/18* | (2006.01) |
| *A45D 33/00* | (2006.01) |
| *A45D 40/00* | (2006.01) |
| *A45D 40/02* | (2006.01) |
| *A61K 8/02* | (2006.01) |
| *A61Q 1/06* | (2006.01) |

(52) U.S. Cl.
    CPC ........... *A45D 33/18* (2013.01); *A45D 33/008* (2013.01); *A45D 40/00* (2013.01); *A61K 8/0237* (2013.01); *A61Q 1/06* (2013.01); *A45D 2040/0012* (2013.01); *A45D 2040/0025* (2013.01)

(58) Field of Classification Search
    CPC ...... A45D 33/18; A45D 33/008; A45D 40/00; A45D 2040/0012; A45D 2040/0025; A61K 8/0237; A61Q 1/06
    See application file for complete search history.

(56) References Cited

FOREIGN PATENT DOCUMENTS

| | | | |
|---|---|---|---|
| EP | 1 882 792 | | 1/2008 |
| JP | 06107523 | * | 4/1994 |
| JP | 06107523 A | * | 4/1994 |
| JP | 2005-313129 | | 11/2005 |
| JP | 2015-119943 | | 7/2015 |
| WO | 03/082603 | | 10/2003 |
| WO | 2014/005265 | | 1/2014 |
| WO | 2017/171245 | | 10/2017 |

OTHER PUBLICATIONS

International Search Report issued Nov. 30, 2021 in International Application No. PCT/IB2021/055445.
Written Opinion of the International Searching Authority issued Nov. 30, 2021 in International Application No. PCT/IB2021/055445.
International Preliminary Report on Patentability issued Feb. 10, 2023 in International Application No. PCT/IB/2021/055445.

* cited by examiner

*Primary Examiner* — Mina Haghighatian
(74) *Attorney, Agent, or Firm* — Wenderoth, Lind & Ponack, L.L.P.

(57) ABSTRACT

A powder cosmetic product in the form of a flat wafer or plate or extruded rod for lipsticks includes a cosmetic body with a visible surface provided with a plurality of protruding stripes with triangular section. Each stripe has a vertex, a first inclined side decorated with a portion of a first image, and a second inclined side decorated with a portion of a second image. By observing the cosmetic body from an observation point (A) angled so that only the first inclined side of each stripe can be seen, only the first image is visible, while by observing the same cosmetic body from an observation point (B) angled so that only the second inclined side of each stripe can be seen, only the second image is visible.

5 Claims, 3 Drawing Sheets

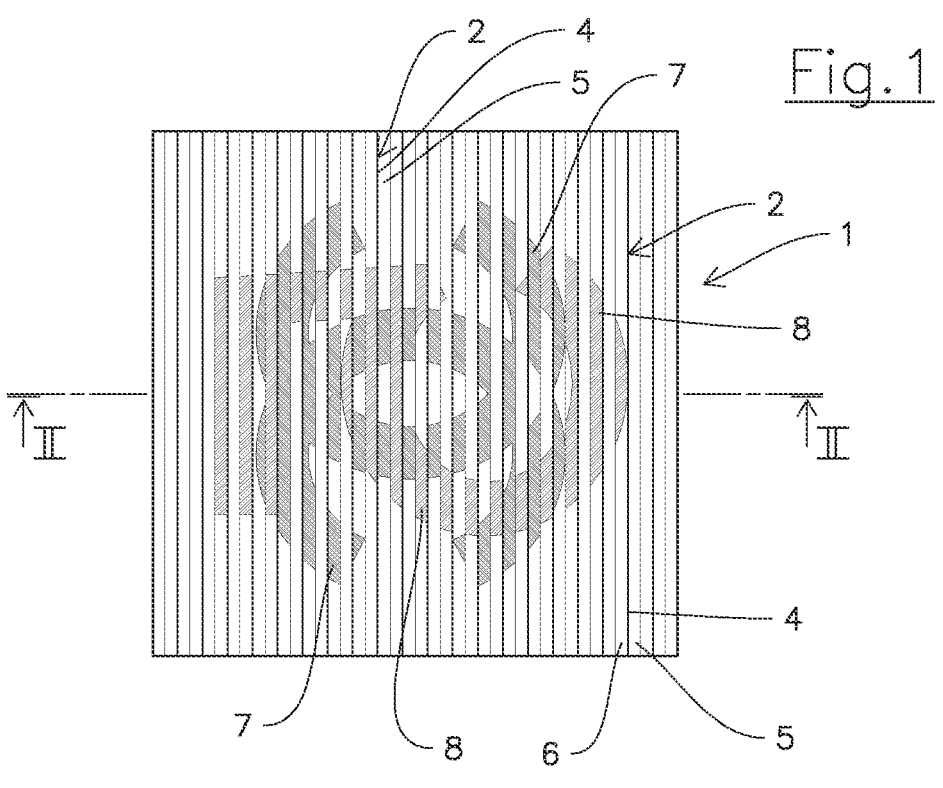
_Fig.1_
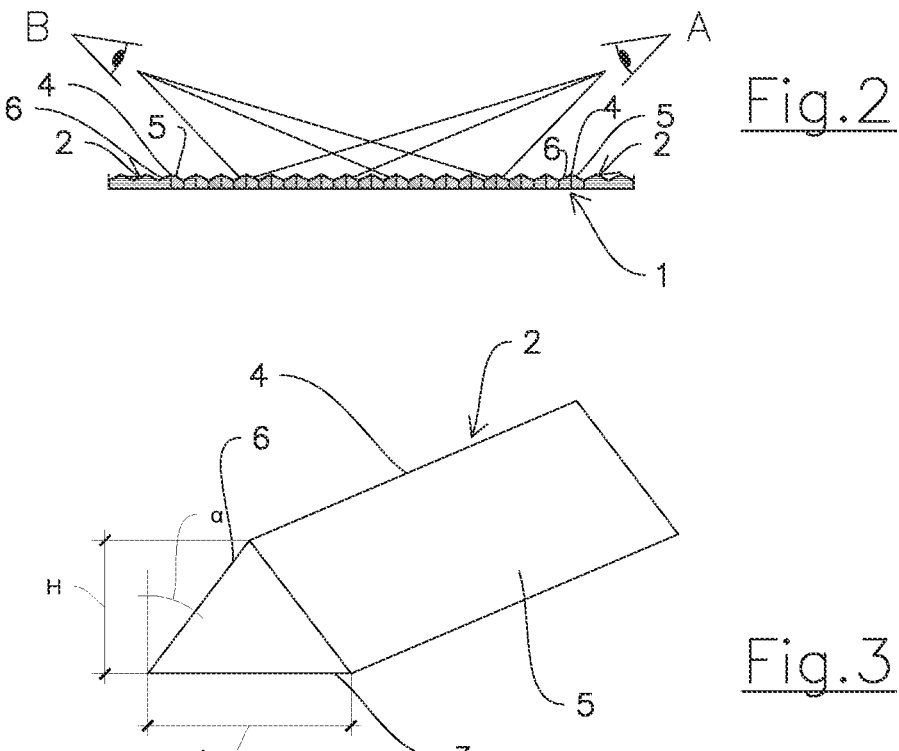
_Fig.2_
_Fig.3_

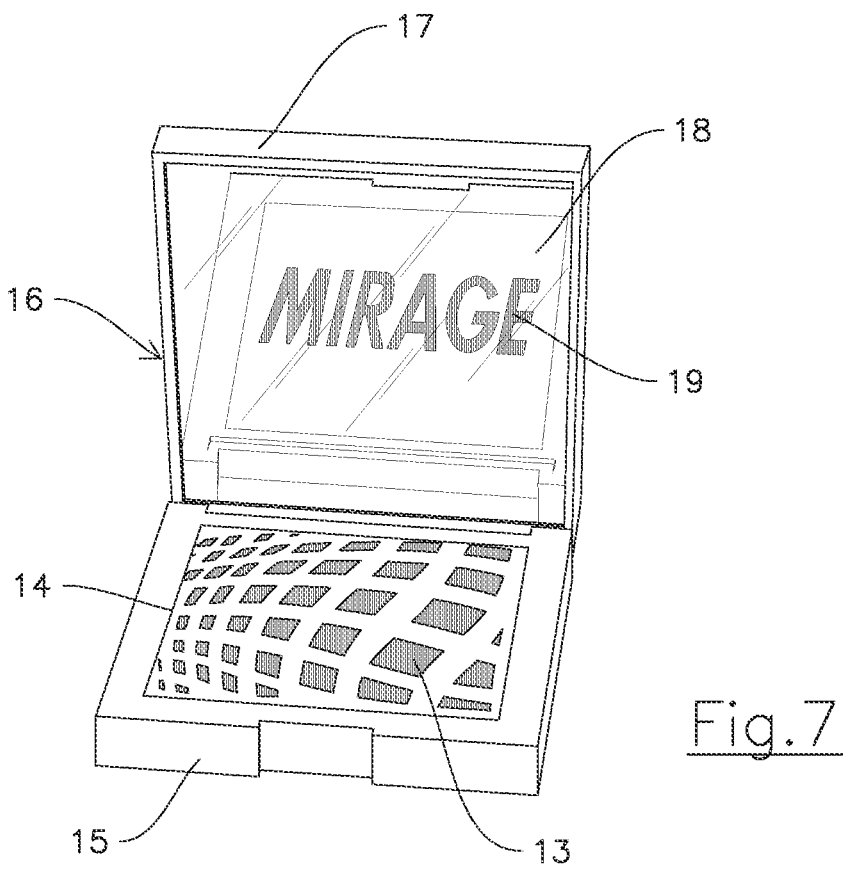
_Fig.7_
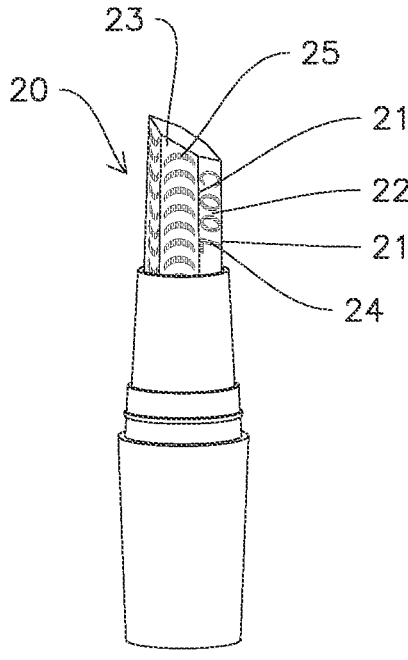
_Fig.8_

COSMETIC PRODUCT WITH SURFACE DECORATION OF DYNAMIC IMAGES

BACKGROUND OF THE INVENTION

The present invention relates to a cosmetic product having a surface decoration consisting of images with a dynamic effect, this term meaning the capacity to show separate images which can vary with the angle of the observation point.

The cosmetic product can be made of pressed, melted, baked powder or it can be in the form of an extruded rod.

The current surface decoration techniques of a cosmetic product allow creating "static" images, i.e., visible in the same manner from any observation point, on the surface thereof.

JP 2005-313129 A discloses the cover body of a compact container in which a base material has a sight surface provided with a plurality of protruding stripes with triangular section. Each stripe has a vertex, a first inclined side decorated with a portion of a first color and a second inclined side decorated with a second color.

SUMMARY OF THE INVENTION

It was the object of the present invention to develop a technique for forming and decorating the surface of a cosmetic product which would give rise to two or more surface images which can be seen separately as a function of the observation point angle.

The aforesaid object is achieved by a cosmetic product made of pressed, or melted and baked, or extruded powder or in the form of a rod or stick, such as a lipstick, having a body with a visible surface consisting of a plurality of protruding stripes with triangular section, each having an upper vertex, a first inclined side decorated with a portion of a first image, and a second inclined side decorated with a portion of a second image.

The shaping of the surface of the cosmetic product, with stripes with triangular section, allows observing the same surface from two different observation points angled so as to make respective sides of the stripes visible without being able to notice the opposite sides.

Thereby, it is possible to decorate the same cosmetic product with two different images which are separately visible from two different observation points, thus obtaining the so-called "lenticular effect".

The inclination of the sides of the stripes, their width and their height must comply with proportion rules, which also depend on the cosmetic product to which the "lenticular" effect is intended to be applied. In particular, the inclination of the sides (or sidewalls) of the stripes must be from 40° to 60°, the base width from 0.5 mm to 3.0 mm, and the height from 0.2 mm to 1.5 mm.

BRIEF DESCRIPTION OF THE DRAWINGS

The features of the present invention will be better understood from the following detailed description of exemplary embodiments shown in the accompanying drawings, in which:

FIG. 1 is a plan view of a cosmetic product with parallel surface stripes and a decoration with a double image according to the present invention;

FIG. 2 is a sectional view according to line II-II in FIG. 1;

FIG. 3 is an enlarged perspective depiction of a surface stripe of the cosmetic body in FIGS. 1 and 2;

FIG. 7 shows a front view of another example of a package including a cosmetic product according to the present invention; and FIG. 8 shows a lipstick applicator including a lipstick rod with the decorative features of the present invention.

DETAILED DESCRIPTION OF THE INVENTION

Figures 4, 5, 6:
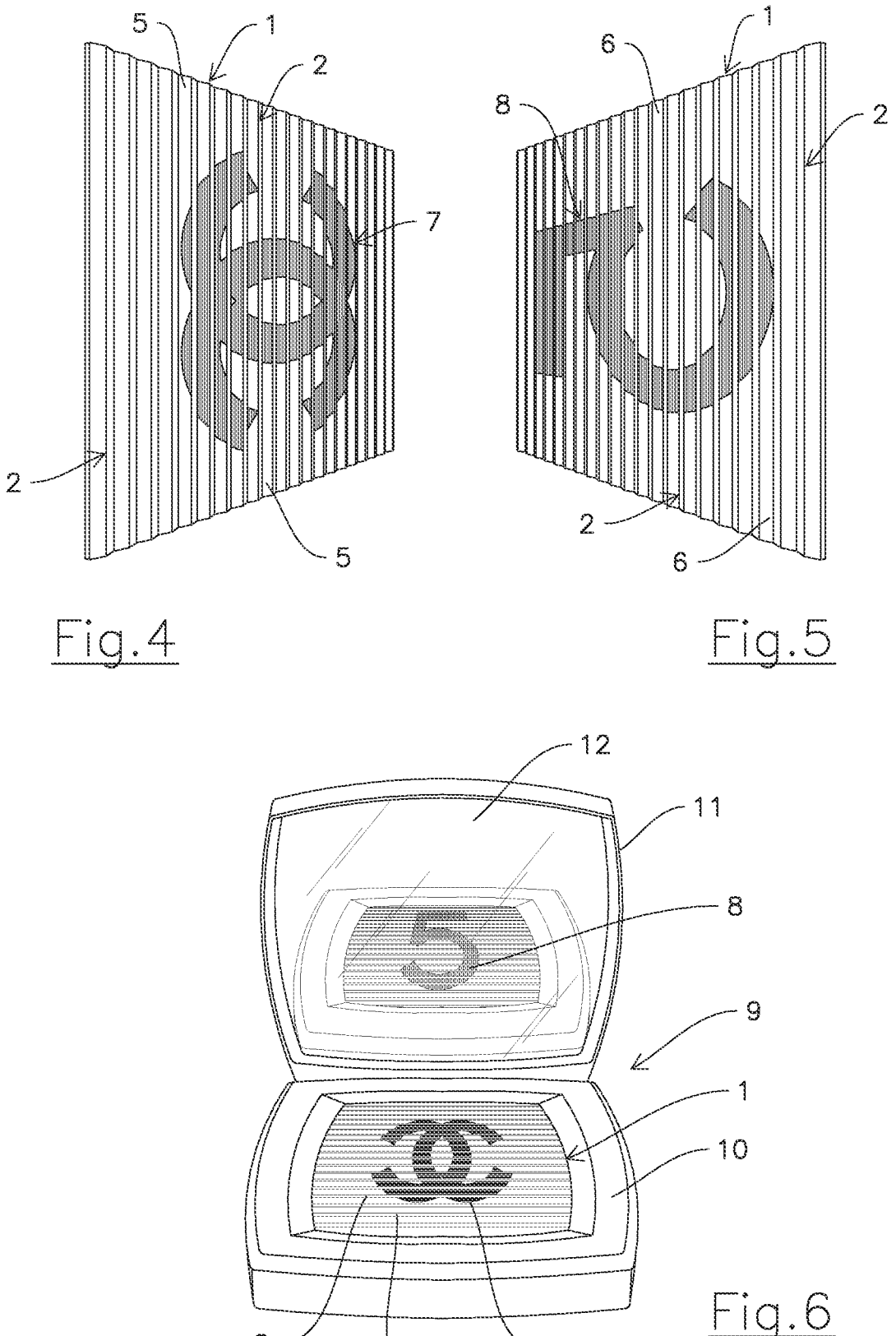
FIGS. 4 and 5 show views of the decorated surface of the cosmetic product from observation points with opposing angles as shown in FIG. 2.
FIG. 6 shows a front view of a box-like package including the cosmetic product in FIG. 1.

The cosmetic product in FIGS. 1 and 2 has a square flat plate- or wafer-shaped body 1 made of pressed, or melted and baked, or extruded cosmetic powder, which has an upper surface shaped so as to have a plurality of protruding stripes 2, by way of example parallel, such as that shown on an enlarged scale in FIG. 3. Obviously, the shape of the plate is completely indifferent, since it could be rectangular, polygonal, circular, elliptical, or any other desired shape without this affecting the scope of the invention.

As indicated in FIG. 3, each stripe 2 has a triangular section with a base 3 of width L, an upper vertex 4 of height H, and inclined lateral sides 5 and 6 with inclination a.

Width L, height H and inclination a of the stripes 2 must comply with proportion rules also depending on the cosmetic product used. In particular, the inclination a must range from 40° to 60°, the base width L must range from 0.5 mm to 3.0 mm, and the height H from 0.2 mm to 1.5 mm.

As shown in FIG. 1, the lateral sides 5 of the triangular stripes 2 are decorated with portions of a first image 7, while the lateral sides 6 of the same triangular stripes are decorated with portions of a second image 8.

The decoration of the surface of the cosmetic product can be obtained by various methods, even as a function of the type of cosmetic product. The following methods can be indicated by way of example:

ink-jet—four-color printing by means of a cosmetic-type ink jet printer;

spray+laser—total covering of the surface with a pearlescent spray and successive laser removal;

engraved die—the images are engraved directly onto the sides of the stripes in the die, thus creating light/dark effects by means of known removal technologies (such as milling, electrical discharge machining, photo-engraving). In this case, the visual effect is created during the step of forming the cosmetic product directly transferring the image of the die onto the product;

laser—the images are engraved directly through the laser technique.

Whichever method is used, due to the inclination of the two sides 5 and 6, looking at the upper surface of the cosmetic plate 1 from opposing observation points A and B angled so as to see only the inclined sides 5 and 6 of the surface (FIG. 2), respectively, it is possible to detect the entire image 7 from point A and the entire image 8 from point B in a separate manner, as shown in FIGS. 4 and 5, respectively.

It results that, by inserting the cosmetic plate 1 into the box-like base 10 of a packaging case 9 with a hinged cover 11 provided with a mirror 12, as shown in FIG. 6, i.e., with the stripes 2 parallel to the rotation axis of the cover 11, it is possible, with the cover open, to observe separately the image 7 inside the base 10 and the image 8 reflected in the mirror 12.

Likewise, it is possible to obtain a package, such as that in FIG. 7, which has a first visible image 13 on the surface of a cosmetic product 14 inserted into the base 15 of a case 16 with hinged cover 17 and mirror 18 and a second image 19 reflected in the mirror 18.

It is also possible to shape the surface of the cosmetic product with stripes not parallel to one another, which are wavy or converging or diverging, whereby the images can also be seen separately by simply rotating the plate or wafer to the right or to the left, not necessarily by using a mirror.

The same inventive principle set forth above for a powder cosmetic product with reference to FIGS. 1-5 and applied, by way of example, to the packages in FIGS. 6 and 7, can be used for decorating a lipstick rod with polygonal section, such as that indicated by reference numeral 20 in FIG. 8. In this case, the vertices of the stripes with triangular section provided by the present invention consist of the corners 21 of the rod 20 and the inclined sides of the stripes consist of the flat faces 22, 23 at the two sides of the corners 21.

The respective images seen from different angles are those indicated by reference numerals 24 and 25.

The invention claimed is:

1. A cosmetic product made of pressed or melted and baked, or extruded powder, or in the form of a rod or stick, the cosmetic product having a sight surface provided with a plurality of protruding stripes, each stripe having a triangular cross-section which includes a first inclined side and a second inclined side, the first and second inclined sides converging towards a vertex, wherein the first inclined side of each stripe includes a respective portion of a first image, and the second inclined side of each stripe includes a respective portion of a second image,

wherein the respective portions of the first image are arranged on the first inclined sides of the plurality of stripes such that when the cosmetic product is viewed from a first observation point which is angled such that only the first inclined side of each stripe is visible, the respective portions of the first image align such that the first image is visible in its entirety, and wherein the respective portions of the second image are arranged on the second inclined sides of the plurality of stripes such that when the cosmetic product is viewed from a second observation point which is angled such that only the second inclined side of each stripe is visible, the respective portions of the second image align such that the second image is visible in its entirety.

2. The cosmetic product according to claim 1, wherein the triangular cross-section of each stripe has a base width from 0.5 mm to 3.0 mm and a height from 0.2 mm to 1.5 mm, and a side inclination of each of the first and second inclined sides is from 40° to 60°.

3. The cosmetic product according to claim 1, wherein the cosmetic product is a flat plate or wafer having the sight surface with the plurality of protruding stripes.

4. The cosmetic product according to claim 1, wherein the cosmetic product is a lipstick rod having a polygonal cross-section.

5. The cosmetic product according to claim 4, wherein the plurality of protruding stripes with triangular section are corners of the rod, and the first and second inclined sides of the plurality of protruding stripes are flat faces which extend to corners from opposite directions.

\* \* \* \* \*